United States Patent [19]
Farng et al.

[11] Patent Number: 5,073,279
[45] Date of Patent: Dec. 17, 1991

[54] SULFUR COUPLED HYDROCARBYL DERIVED MERCAPTOBENZOTHIAZOLE ADDUCTS AS MULTIFUNCTIONAL ANTIWEAR ADDITIVES AND COMPOSITIONS CONTAINING SAME

[75] Inventors: Liehpao O. Farng, Lawrenceville; Andrew G. Horodysky, Cherry Hill, both of N.J.; James G. Murray, Whiting, Vt.

[73] Assignee: Mobil Oil Corporation, Fairfax, Va.

[21] Appl. No.: 413,150

[22] Filed: Sep. 27, 1989

[51] Int. Cl.$^5$ .................................... C10M 135/136
[52] U.S. Cl. .................... 252/47; 252/47.5; 548/157; 548/158
[58] Field of Search ............... 252/47, 47.5; 548/157, 548/158

[56] References Cited

U.S. PATENT DOCUMENTS

| | | | |
|---|---|---|---|
| 2,963,432 | 12/1960 | Little et al. | 252/47 |
| 2,963,433 | 12/1960 | Little et al. | 252/47 |
| 3,154,490 | 10/1964 | Rai et al. | 252/47 |
| 3,175,974 | 3/1965 | Rai et al. | 252/47 |
| 3,211,651 | 10/1965 | Elliott et al. | 252/46.7 |
| 3,220,955 | 11/1965 | Kramer et al. | 252/391 |
| 3,407,140 | 10/1968 | Chiddix | 252/47.5 |
| 4,141,845 | 2/1979 | Yaffe | 252/47 |
| 4,487,706 | 12/1984 | Lam | 252/47 |
| 4,740,322 | 4/1988 | DiBiase | 252/45 |
| 4,764,298 | 8/1988 | Croudace | 252/47 |
| 4,873,346 | 10/1989 | Anderson | 548/157 |

FOREIGN PATENT DOCUMENTS

| | | |
|---|---|---|
| WO88/09804 | 12/1988 | European Pat. Off. |
| 90310004.8 | 2/1991 | Netherlands . |
| 676712 | 7/1952 | United Kingdom . |
| 766690 | 1/1957 | United Kingdom . |
| 936755 | 9/1963 | United Kingdom . |
| 1044147 | 9/1966 | United Kingdom . |

OTHER PUBLICATIONS

CA 71(18:82174n.
CA 70(4):12295h.

*Primary Examiner*—Prince Willis, Jr.
*Assistant Examiner*—Jerry D. Johnson
*Attorney, Agent, or Firm*—Alexander J. McKillop; Charles J. Speciale; Howard M. Flournoy

[57] ABSTRACT

Sulfur-coupled hydrocarbyl derived mercaptobenzothiazole adducts have been found to be effective multifunctional antiwear additives for fuels and lubricants.

44 Claims, No Drawings

SULFUR COUPLED HYDROCARBYL DERIVED MERCAPTOBENZOTHIAZOLE ADDUCTS AS MULTIFUNCTIONAL ANTIWEAR ADDITIVES AND COMPOSITIONS CONTAINING SAME

BACKGROUND OF THE INVENTION

Lubricants, such as lubricating oils and greases, are subject to oxidative deterioration at elevated temperatures or upon prolonged exposure to the elements. Such deterioration is evidenced, in many instances, by an increase in acidity and in viscosity, and when the deterioration is severe enough, it can cause metal parts to corrode. Additionally, severe oxidation leads to a loss of lubrication properties, and in especially severe cases this may cause complete breakdown of the device being lubricated.

Antioxidants or oxidation inhibitors are used to minimize the effects of oil deterioration that occur when hot oil is contacted with air. The degree and rate of oxidation will depend on temperature, air and oil flow rates and, of particular importance, on the presence of metals that may catalytically promote oxidation.

Water (moisture) is another critical problem. In spite of even extraordinary precautionary efforts water is found as a film or in minute droplets in vessels containing various hydrocarbon distillates. This brings about ideal conditions for corrosion and damage of metal surfaces of the vessels and the materials contained therein. Also in the lubrication of internal combustion engines quantities of water are often present as a separate phase within the lubricating system. Another serious problem in respect to metallic surfaces in contact with adjacent metallic surfaces is the surface wear caused by the contact of such surfaces. One material capable of simultaneously effectively coping with such problems as these is highly desireous.

The use of sulfur-containing compositions such as sulfurized isobutylenes has been well known for their antiwear properties in a variety of lubricant applications as exemplified by U.S. Pat. Nos. 3,703,504; 3,703,505, and 3,873,454. It has now been found that sulfur-coupled hydrocarbyl derived mercaptobenzothiazole adducts provide exceptional multifunctional antiwear, antioxidant and friction reducing properties. These remarkable benefits are to be expected for a variety of synthetic and mineral oil based lubricants and also for liquid hydrocarbon fuels.

To the best of our knowledge, these compositions have not been previously used as multifunctional additives in lubricating oils, greases, or fuel applications. The additive products themselves and lubricant compositions thereof are both believed to be novel.

SUMMARY OF THE INVENTION

This invention is directed to sulfur-coupled, hydrocarbyl-derived mercaptobenzothiazole adducts made, for example, by reaction of (a) a long-chain olefin such as 1-octadecene or 1-decene with (b) a suitable sulfur source such as sulfur monochloride or sulfur dichloride followed by coupling with (c) a mercaptobenzothiazole and which have been found to exhibit excellent multifunctional antiwear, antioxidant and copper corrosivity performance characteristics when blended in additive concentrations of 0.0001% to 10% wt into fuels or lubricants. This application is, therefore, also directed to lubricant and fuel compositions containing additive concentrations of the embodied novel sulfur- containing adducts.

Although applicants wish not to be bound by any particular theory, the hydrocarbyl groups, sulfur moieties and heterocyclic rings are each believed to provide the basis for synergistic antiwear, antioxidant, copper passivating and friction reducing properties. The hydrocabyl group is believed to provide the lubricity/friction reducing and/or detergency properties. The sulfur-coupling groups provide additional antiwear and antioxidant characteristics. The benzothiazole group may additionally contribute antioxidant, lubricity and high-temperature stabilizing properties to this new class of additives.

All of these beneficial properties are believed to be enhanced as a result of this novel internal synergism. This unique internal synergism concept is believed to be applicable to similar structures containing (a) hydrocarbyl groups, (b) sulfur-coupling groups and (c) benzothiazole linkages within the same molecule.

DESCRIPTION OF SPECIFIC EMBODIMENTS

Generally speaking, long-chain olefins maybe reacted with a sulfur halide such as sulfur monochloride followed by a coupling reaction with, for example, 2-mercaptobenzothiazole, optionally in the presence of a phase transfer catalyst and organic or inorganic bases, such as sodium or potassium hydroxide, in a one pot, two step, coupling reaction sequence (addition step followed by substitution step) to form a mixture of reaction products. We believe the following type of product prepared as disclosed below is included in the mixture, along with related isomers and other possible reaction products:

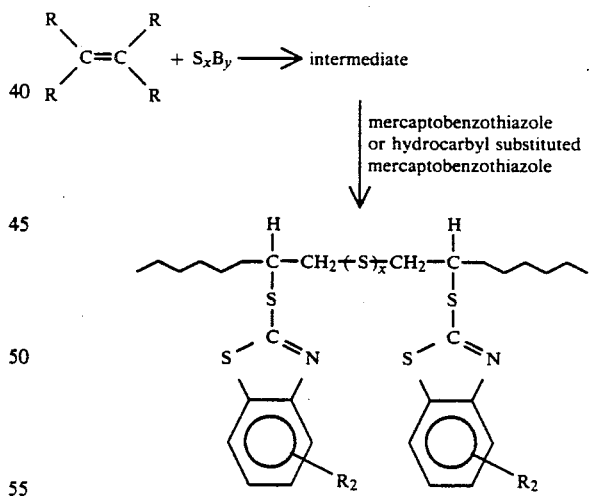

where each R is independently hydrogen or $C_1$–$C_{40}$ hydrocarbyl, preferably the sum of all R groups equals 4 or more carbon atoms and more preferably the sum of all R groups is equal to 10 or more carbon atoms, B is halogen, preferably chlorine, x is an integer from 1 to 8 and y is an integer from 1 to 2. $R_2$ is hydrogen or $C_1$–$C_{40}$ hydrocarbyl. R or $R_2$ can optionally contain sulfur, nitrogen and/or oxygen.

An excess of one reagent or another can be used. Mixtures can be used. Molar quantities, less than molar quantities, or more than molar quantities of any of the reactants can be effectively used.

Suitable long chain hydrocarbyl olefins include but are not limited to $C_6$ to about $C_{60}$ and preferably $C_8$ to about $C_{32}$ olefins such as octene, decene and octadecene or mixtures thereof. Preferred are 1-decene and octadecene. Internal olefins and terminal olefins are suitable as well as linear and branched olefins. Optionally the olefins may be substituted with nitrogen, sulfur, and/or oxygen.

Suitable mercaptobenzothiazoles include but are not limited to 2-mercaptobenzothiazole, 2-mercapto 6-methylbenzothiazole, 2-mercapto 5-nitrobenzothiazole and derivatives or mixtures thereof.

Suitable phase transfer/catalytic agents include but are not limited to quaternary ammonium salts such as benzyltriethylammonium chlorides, cylic polyethers, poly(ethylene oxides), polyether-amines where the amine is a tertiary-amine or mixture thereof and the like. However, as previously noted the use of a phase tranfer catalyst is optional. Preferred are trihydrocarbyl ammonium chlorides such as tricaprylyl methylammonium chloride. Solvents can also be used to improve reaction rates. Generally, they are non-reactive hydrocarbon solvents such as toluene or a xylene.

Any suitable inorganic or organic base may be used herein. Preferred are sodium hydroxide, potassium hydroxide and organic bases such as ammonium hydroxide or triethylamine.

Generally speaking the various reaction times, temperatures, pressures and quantities of reactive materials may vary widely and are not believed to be critical.

Generally the temperature may vary from about 30° to about 250° C. with 70° to 150° C. being preferable; the pressure may vary from ambient or autogenous or slightly higher. Reduced pressure can also be used if desired. The molar ratio of reactants may vary from about 1:10 to about 10:1 of sulfurized olefin to mercaptobenzothiazole. Preferred is a molar ratio of 1:2 to about 2:1.

The time will vary depending upon the specific reactants and if a solvent or catalyst is used from about 0.5 hours up to about 24 hours or more.

The additives may be incorporated into any suitable lubricating media which comprises oils of lubricating viscosity, e.g., mineral or synthetic; or mixtures of mineral and synthetic or greases in which the aforementioned oils are employed as a vehicle or into such functional fluids as hydraulic fluids, brake fluids, power transmission fluids and the like. In general, mineral oils and/or synthetic oils, employed as the lubricant oil, or grease vehicle may be of any suitable lubricating viscosity range, as for example, from about 45 SSU at 100° F. to about 6000 SSU at 100° F., and, preferably, from about 50 to about 250 SSU at 210° F. These oils may have viscosity indices from below zero to about 100 or higher. Viscosity indices from about 70 to about 95 are preferred. The average molecular weight of these oils may range from about 250 to about 800.

Where the lubricant is to be employed in the form of a grease, the lubricating oil is generally employed in an amount sufficient to balance the total grease composition, after accounting for the desired quantity of the thickening agent and other additive components to be included in the grease formulation.

When high temperature stability is not a requirement of the finished grease, mineral oils having a viscosity of at least 40 SSU at 150° F., and particularly those falling within the range from about 60 SSU to about 6,000 SSU at 100° F. may be employed. The lubricating vehicles of the improved greases of the present invention, containing the above described additives, are combined with a grease forming quantity of a thickening agent. For this purpose, a wide variety of materials dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickners may be employed which do not melt and dissolve when used at the required temperature within a particular environment; soap thickeners such as metallic (lithium or calcium) soaps including hydroxy stearate and/or stearate soaps can be used however, in all other respects, any material which is normally employed for thickening or gelling hydrocarbon fluids or forming greases can be used in preparing the aforementioned improved greases in accordance with the present invention.

In instances where synthetic oils are desired in preference to mineral oils, or in combination therewith, various compounds of this type may be successfully utilized as the vehicle for the grease. Typical synthetic vehicles include polyisobutylene, polybutenes, hydrogenated polydecenes, polypropylene glycol, polyethylene glycol, trimethylolpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers, etc.

As has been disclosed hereinabove, the reaction products are useful as multifunctional antiwear/antioxidant-/antirusts agents in lubricants and fuels. They are added to the lubricating medium or fuel in amounts sufficient to impart such properties thereto. More particularly, such properties will be imparted to lubricants by adding from about 0.001% to about 10% by weight, preferably from about 0.01% to about 3% by weight of the neat product and to fuels, by adding from about 5 to 1,250 pounds per thousand barrels of fuel, preferably from about 50 to 150 pounds per 1000 barrels.

Suitable fuels include but are not limited to liquid hydrocarbon fuels such as gasolines, alcohol and mixtures thereof such as gasohol, distillate fuel oils, diesel fuel and heating fuel oil, and the like.

The products of the present patent application show good stability and compatibility when used in the presence of other commonly used lubricant or fuel additives. Therefore, fully formulated lubricating oils may include a variety of additives (for their known purpose) such as dispersants, detergents, inhibitors, antiwear agents, antioxidant, antifoam, antirust, demulsifier, pour depressant and other additives including phenates, sulfonates and zinc dithiophosphates, polymers, polyisobutylsuccinimides, arylamines, hindered phenols, esters, amides, etc.

The following examples are exemplary only and are not intended as limitations.

EXAMPLE 1

Octadecene-1/Sulfur Monochloride Adduct

Approximately 840 gm (3.0 mol. 90% purity) of octadecene was charged into a 2-liter reactor equipped with dropping funnel, reflux condenser, thermometer, and mechanical stirrer. Approximately 202.5 gm (1.5 mol.) of sulfur monochloride was added through the dropping funnel. Then the reaction mixture was heated to 95° to 100° C. to activate the sulfochlorination reaction. Moderate exotherm brought the temperature to 113° C. then the reaction was held at 110° C. for four hours. Near the end of the period at 110° C., the color became dark reddish. At completion, the product was left to cool slowly. This produced approximately 103 gm liquid material ($C_{36}H_{72}S_2Cl_2$).

EXAMPLE 2

Octodencene-1/Sulfur Monochloride/2-Mercaptobenzothiazole Adduct 278.4 gm of the product of Example 1 (0.4 mol.), 133.8 gm of 2-mercaptobenzothiazole (0.8 mol.), 8 gm of Aliquat 336 (phase transfer catalyst obtained from Aldrich Chemical Company: tricaprylylmethyl ammonium chloride), 200 ml caustic solution (32 gm sodium hydroxide dissolved in 200 ml water), and 400 ml toluene were mixed in a 2-liter reactor. The reactants were stirred under reflux for six hours, and then cooled to ambient temperature. The aqueous phase was separated, and the organic phase was twice washed with 400 ml of water. Thereafter, toluene was removed by vacuum distillation leaving a dark fluid as the desired product (373 gm). It was further purified by hot filtration through Super-Cel.

Nitrogen analysis: 2.4%.
Sulfur analysis: 19.2%.

EXAMPLE 3

In the Absence of Phase Transfer Catalyst 33.4 gm of 2-mercaptobenzothiazole (0.2 mol.) was suspended in 150 ml toluene and caustic solution (8 gm sodium hydroxide dissolved in 20 ml water). Approximately 69.6 gm of the product of Example 1 (0.2 mol.), and 20 ml of dimethyformamide (DMF) were added. The reactants were stirred under reflux for three to four hours and a small amount of solid gradually precipitated from the dark brown mixture. Then, the cooled mixture was washed with 100 ml portion of water three times. The organic phase was evaporated at reduced pressure and elevated temperature (130° C.) to remove volatile materials to afford the final product as a dark brownish oil (70.2 gm).

Nitrogen analysis: 2.09%.
Sulfur analysis: 17.2%.

EXAMPLE 4

The procedure of Example 3 was followed with only one exception: dimethylsulfoxide (DMSO) (20 ml) was used instead of dimethylformamide (DMF) (20 ml).

EXAMPLE 5

The procedure of Example 2 was followed at small scale, i.e., the same ratios of materials were used but the quantities of each were about ⅜ less.

Nitrogen analysis: 2.56%.
Sulfur analysis 19.2%.

EXAMPLE 6

Decene-1/Sulfur Dichloride/2-Mercaptobenzothiazole Adduct

The procedure of Examples 1 and 2 were followed with the following exceptions: Decene-1 and sulfur dichloride were used instead of octadecene-1 and sulfur monochloride.

Sulfur analysis: 25.4%.

Evaluation of Product

The products of selected examples were evaluated in the Catalytic Oxidation Test to determine antioxidant activity when blended at additive concentrations in lubricants as shown in Table I.

CATALYTIC OXIDATION TEST

The test lubricant composition is subjected to a stream of air which is bubbled through the composition at a rate of 5 liters per hour at the specified temperature for the required number of hours. Present in the composition (comprising a 200 second solvent refined paraffinic neutral oil) in addition to the additive compound were metals commonly used as materials to construct engines namely:

(a) 15.6 square inch of sand-blasted iron wire;
(b) 0.78 square inch of polished copper wire;
(c) 0.87 square inch of polished aluminum wire; and
(d) 0.107 square inch of polished lead surface.

The test results are reported below in Table I.

TABLE I

| | Catalytic Oxidation Test (325° F., 40 Hours) | | |
|---|---|---|---|
| | Percent Change in Viscosity % Δ KV | Change in Acid Number Δ TAN | Pb Loss (mg) |
| Base Oil (200 Second Solvent Paraffinic Neutral Lubricating oil) | 57.9 | 4.78 | 2.9 |
| 1% Example 5 | 27.7 | 1.47 | 2.1 |
| 1% Example 6 | 38.3 | 2.03 | 0.0 |

As confirmed by the good control of (a) increase in viscosity, (b) increase in acid number and (c) lead loss, these sulfur-coupled hydrocarbyl-derived mercaptobenzothiazole adducts demonstrate remarkable antioxidant properties.

The products of the examples were also blended into mineral oil and evaluated for antiwear activity using the Four-Ball Wear Test. Test results were as shown in Table II.

The Four-Ball Wear Test (ASTM D2266)

In this test, three stationary balls are placed in a lubricant cup and a lubricant containing the additive to be tested in added thereto. A fourth ball is place on a chuck mounted on a device which can be used to spin the ball at known speeds and loads. Various percentages by weight of each product was placed in the blend. The samples were tested at 200° F. and 300° F. at a load of 60 kilograms and 2000 rpm for 30 minutes.

TABLE II

| Four-Ball Wear Test (2,000 rpm, 60 kg load, 30 Minutes) | | |
|---|---|---|
| | Wear Scar Diameter, mm | |
| | at 300° F. | at 200° F. |
| Base Oil (80% Solvent Paraffinic Bright, 20% Solvent Paraffinic Neutral Lubricating Oils.) | 4.11 | 3.20 |
| 1% of Example 2 in above Base Oil | | 0.84 |
| 1% of Example 3 in above Base Oil | 1.69 | 0.79 |
| 1% of Example 4 in above Base Oil | 1.60 | 1.55 |
| 1% of Example 5 in above Base Oil | 1.70 | 0.82 |
| 1% of Example 6 in above Base Oil | 1.87 | 0.96 |

The Four-Ball Wear Test results clearly demonstrate the superior antiwear properties of these compositions.

It should be noted that the Four-Ball Wear Test is also a test which indicates or predicts the properties of these additives in fuels.

The products of selected examples were further blended into 200 second solvent paraffinic neutral lubricating oil and evaluated for control of copper corrosivity using the ASTM D130 Copper Strip Corrosion Test. Test data is shown in Table III.

TABLE III

| ASTM D130 Copper Strip Corrosion Test (250° F., 3 Hours) | |
|---|---|
| | Rating |
| Base Oil (200 Second Solvent Paraffinic Neutral Lubricating Oil) | 1A |
| 1% of Example 2 in above Base Oil | 2B |
| 1% of Example 3 in above Base Oil | 1B |

Corrosion Test Rating
1 represents zero to slight tarnish;
2 represents moderate tarnish;
A & B represent shading within numerical grade.

The above test results show the good control of copper corrosivity exhibited by these sulfur-containing compositions.

The use of additive concentrations of sulfur-coupled hydrocarbyl derived mercaptobenzothiazole adducts, in accordance with the present invention, in premium quality automotive and industrial lubricants and fuels will significantly enhance their performance, improve stability and extend service life. These novel compositions described in this patent application are useful at low concentrations and do not contain any potentially undesirable metals or phosphorus. These multifunctional antioxidants and antiwear additives can be commercially made using an economically favorable process.

Although the present invention has been described with preferred embodiments, it is to be understood that modifications and variations may be utilized without departing from the spirit and scope of this invention, as those skilled in the art will readily understand. Such modifications and variations are considered to be within the purview and scope of the appended claims.

What is claimed is:

1. A composition comprising a major amount of an oil of lubricating viscosity or grease prepared therefrom and a minor multifunctional antioxidant, antiwear, anticorrosion amount of from about 0.001 to about 10 wt. % based on the total weight of the composition of an additive reaction product comprising a sulfur coupled hydrocarbyl mercaptobenzothiazole made by (a) reacting a $C_6$–$C_{60}$ long-chain olefin with (b) a sulfur reactant and thereafter reacting the sulfur coupled intermediate product of (a) and (b) with (c) a mercaptobenzothiazole and wherein the molar quantities of the sulfurized olefin products of (a) and (b) to mercaptobenzothiazole vary from about 1:10 to about 10:1 and the temperature varies from ambient to about 250° C. with ambient or autogenous pressure and wherein the sulfur coupled hydrocarbyl mercaptobenzothiazole product has the following generalized structure:

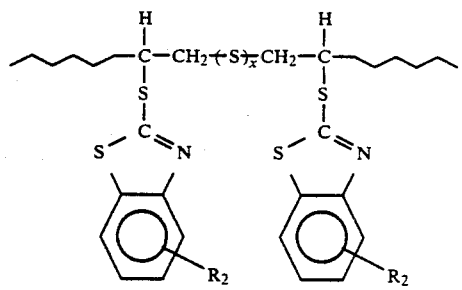

wherein $R_2$ is hydrogen or $C_1$–$C_{40}$ hydrocarbyl and optionally contains sulfur, nitrogen and/or oxygen and x is an integer of from 1 to about 8.

2. The composition of claim 1 wherein said olefin is a linear olefin.

3. The composition of claim 1 wherein said olefin is a branched olefin.

4. The composition of claim 1 wherein said olefin is a terminal olefin.

5. The composition of claim 1 wherein said long-chain olefin is selected from olefins having the following generalized structure:

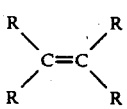

where each R is hydrogen or $C_1$ to about $C_{40}$ with the proviso that the sum of the carbon atoms of the R groups equals at least 4, and said sulfur source is selected from sulfur monochloride and sulfur dichloride.

6. The composition of claim 1 wherein said reaction product is formed in the presence of a phase transfer catalyst.

7. The composition of claim 6 wherein said phase transfer catalyst is selected from quaternary ammonium salts.

8. The composition of claim 7 wherein said phase transfer catalyst is tricaprylylmethyl ammonium chloride.

9. The composition of claim 1 wherein said reaction product is formed in the absence of a phase transfer agent.

10. The composition of claim 1 wherein said additive product is octadecene-1/sulfur monochloride/2-mercaptobenzothiazole adduct.

11. The composition of claim 1 wherein said additive product is decene-1/sulfur dichloride/2-mercaptobenzothiazole adduct.

12. The composition of claim 7 wherein said additive product is octadecene-1/sulfur monochloride/2-mercaptobenzothiazole adduct.

13. The composition of claim 7 wherein said additive product is decene-1/sulfur dichloride/2-mercaptobenzothiazole adduct.

14. The composition of claim 9 wherein said additive product is octadecene-1/sulfur monochloride/2-mercaptobenzothiazole adduct.

15. The composition of claim 9 wherein said additive product is decene-1/sulfur dichloride/2-mercaptobenzothiazole adduct.

16. The composition of claim 1 wherein said composition comprises an oil of lubricating viscosity selected from mineral oils, synthetic oils and mixtures thereof.

17. The composition of claim 16 wherein said oil is a mineral oil.

18. The composition of claim 16 wherein said oil is a synthetic oil.

19. The composition of claim 16 wherein said oil is a mixture of synthetic and mineral oils.

20. The composition of claim 1 wherein said composition is a grease composition.

21. A product of reaction comprising a sulfur coupled hydrocarbyl mercaptobenzothiazole made by reacting (a) a $C_6$ to about $C_{60}$ long-chain olefin with (b) a sulfur reactant and thereafter reacting the sulfur coupled intermediate product of (a) and (b) with (c) a mercaptobenzothiazole and wherein the molar quantities of the sulfurized olefin product of (a) and (b) to mercaptobenzothiazole vary from 1:10 to about 10:1 and the temperature varies from ambient to about 250° C. with ambient or autogenous pressure and wherein the hydrocarbyl mercaptobenzothiazole product has the following generalized structure:

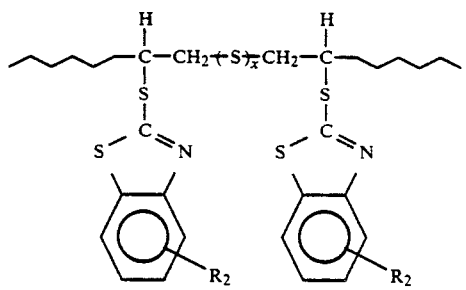

wherein $R_2$ is hydrogen or $C_1$–$C_{40}$ hydrocarbyl and optionally contains sulfur, nitrogen and/or oxygen and x is an integer of from 1 to about 8.

22. The product of claim 21 wherein said olefin is a branched olefin.

23. The product of claim 21 wherein said olefin is a linear olefin.

24. The product of claim 21 wherein said olefin is a terminal olefin.

25. The product of claim 21 wherein (a) said long chain olefin has the following generalized structure:

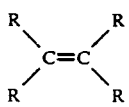

where R is hydrogen or $C_1$ to about $C_{40}$ hydrocarbyl with the proviso that the sum of the carbon atoms of the R groups equals at least 4, and where (b) said sulfur reactant has the following generalized structure:

where B is halogen, x is an integer of from 1 to about 8, and y is an integer of from 1 to about 2 and said mercaptobenzothiazole is a 2-mercaptobenzothiazole.

26. The product of claim 25 wherein said long chain olefin has from 6 to about 60 carbon atoms, said sulfur reactant is selected from sulfur monochloride or sulfur dichloride.

27. The product of claim 21 where said reaction product is formed in the presence of a phase transfer catalyst.

28. The product of claim 27 where said catalyst is a quaternary ammonium salt.

29. The product of claim 28 where said catalyst is tricaprylylmethyl ammonium chloride.

30. The product of claim 21 where the reactants are (a) octadecene-1, (b) sulfur monochloride and (c) 2-mercaptobenzothiazole.

31. The product of claim 21 where the reactants are (a) decene-1 (b) sulfur dichloride and (c) 2-mercaptobenzothiazole.

32. The product of claim 21 where the reaction product is formed in the presence of a phase transfer catalyst.

33. The product of claim 32 where said phase transfer catalyst is tricaprylylmethyl ammonium chloride.

34. The product of claim 30 where the reaction product is formed in the absence of a phase transfer catalyst.

35. A process for preparing a lubricant additive product comprising a sulfur coupled hydrocarbyl mercaptobenzothiazole adduct prepared by reacting (a) $C_6$ to about $C_{60}$ long chain olefin having the following generalized structure:

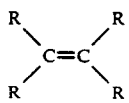

where each R is $C_1$ to about $C_{40}$ hydrocarbyl or hydrogen and where the sum of the R's is at least 4 or more, (b) with a sulfur reactant having the following generalized structure:

where B is halogen, x is an integer of from 1 to about 8, and y is an integer of from 1 to about 2 and thereafter reacting the sulfur coupled intermediate product of (a) and (b) with (c) a mercaptobenzothiazole and wherein said intermediate product is reacted in molar ratios of about 1:10 to about 10:1 to mercaptobenzothiazole and wherein the temperature varies from ambient to about 250° C. with ambient or autogenous pressure and with the reaction time varying from about 0.5 to about 24 hours and wherein the hydrocarbyl mercaptobenzothiazole product has the following generalized structure:

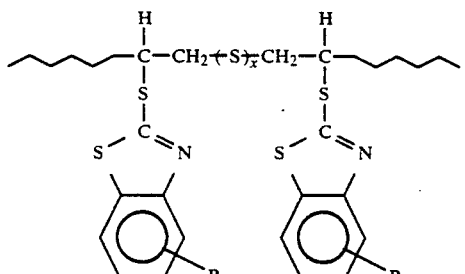

wherein $R_2$ is hydrogen or $C_1$-$C_{40}$ hydrocarbyl and optionally contains sulfur, nitrogen and/or oxygen and x is an integer of from 1 to about 8.

36. The process of claim 35 wherein said olefin is a linear olefin.

37. The process of claim 35 wherein said olefin is a branched olefin.

38. The process of claim 35 wherein said olefin is a terminal olefin.

39. The process of claim 35 wherein said long chain olefin has from 6 to about 60 carbon atoms, said sulfur reactant is sulfur monochloride or sulfur dichloride and said mercaptobenzothiazole is a 2-mercaptobenzothiazole.

40. The process of claim 35 wherein (a) is octadecene-1, (b) is sulfur monochloride and (c) is 2-mercaptobenzothiazole.

41. The process of claim 35 wherein additionally present during the reaction is a phase transfer catalyst.

42. The process of claim 41 wherein said catalyst is tricaprylylmethyl ammonium chloride.

43. The process of claim 35 wherein (a) is decene-1, (b) is sulfur dichloride and (c) is 2-mercaptobenzothiazole.

44. A method of improving the lubricity and fuel economy of internal combustion engines, comprising contacting the moving parts thereof of with a lubricant containing minor amounts of an additive product as claimed in claim 21.

* * * * *